United States Patent [19]

Schneck

[11] Patent Number: 5,350,064

[45] Date of Patent: Sep. 27, 1994

[54] DISPOSABLE CONTAINER FOR CLEANING AND LUBRICATING A DENTAL HANDPIECE

[75] Inventor: Gary G. Schneck, Algonquin, Ill.

[73] Assignee: Gendex Corporation, Des Plaines, Ill.

[21] Appl. No.: 73,274

[22] Filed: Apr. 16, 1993

Related U.S. Application Data

[63] Continuation-in-part of Ser. No. 20,659, Feb. 22, 1993, Pat. No. 5,316,590.

[51] Int. Cl.⁵ ............................................. B65D 83/02
[52] U.S. Cl. ..................................... 206/368; 134/92; 134/182; 433/104
[58] Field of Search ..................... 134/22.1, 26, 32, 42, 134/92, 93, 94.1, 95.1, 182; 433/104, 116; 206/368

[56] References Cited

U.S. PATENT DOCUMENTS

| | | | |
|---|---|---|---|
| 4,218,216 | 8/1980 | Sugai et al. | 433/104 |
| 4,424,036 | 1/1984 | Lokken | 433/116 |
| 4,446,967 | 5/1984 | Halkyard | 206/368 |
| 4,990,087 | 2/1991 | De Rocchis et al. | 433/104 |
| 5,139,142 | 8/1992 | Simon | 206/368 |
| 5,184,718 | 2/1993 | Albert | 134/93 X |

Primary Examiner—Richard O. Dean
Assistant Examiner—Saeed T. Chaudhry
Attorney, Agent, or Firm—Trexler, Bushnell, Giangiorgi & Blackstone, Ltd.

[57] ABSTRACT

A novel disposable container and method is used for cleaning and lubricating a standard dental handpiece. The disposable container completely encloses a head of the dental handpiece. When the handpiece is cleaned or lubricated with cleaning or lubricating agents, the container collects cleaning or lubricating agents and any other materials that are expelled therewith from the handpiece to prevent these materials from entering the atmosphere.

17 Claims, 2 Drawing Sheets

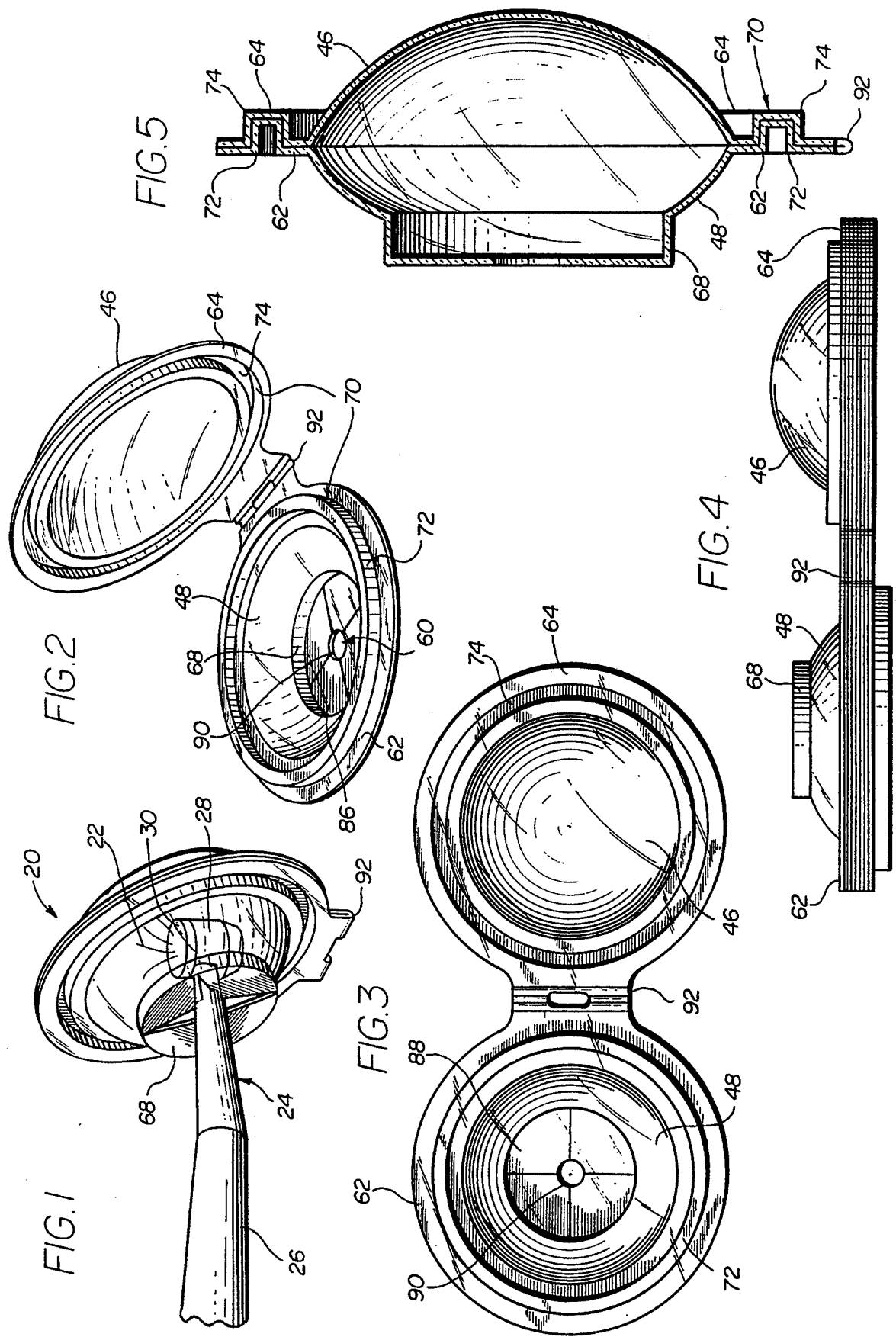

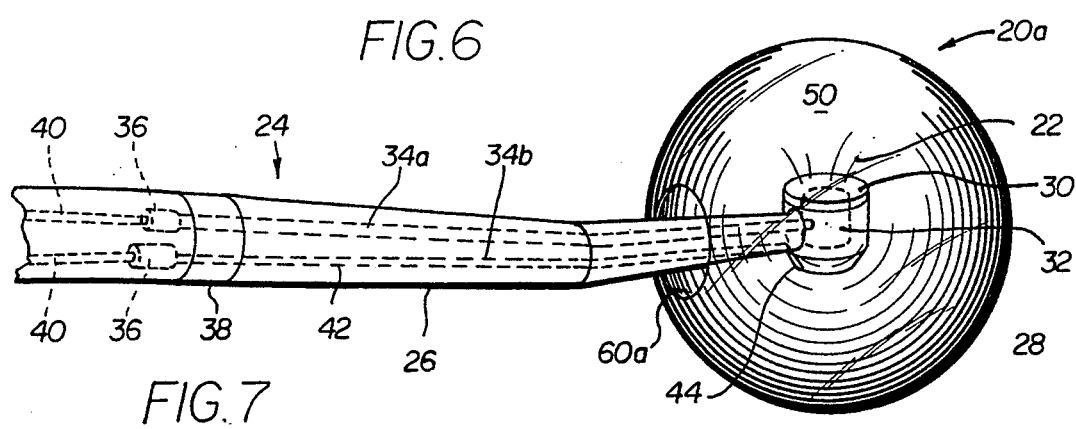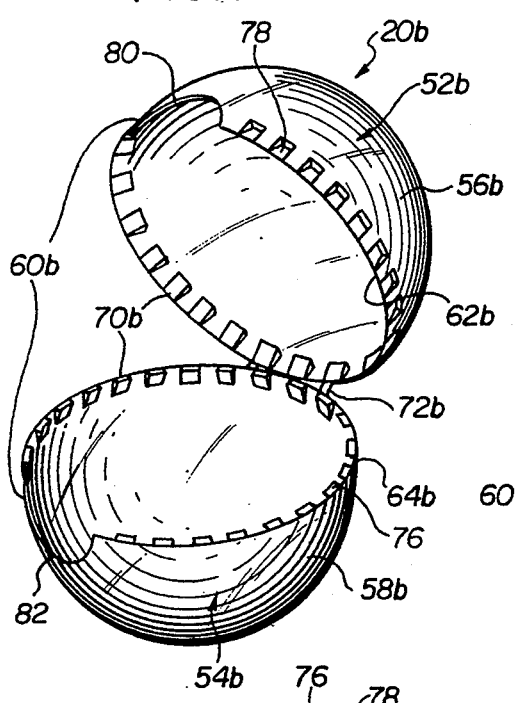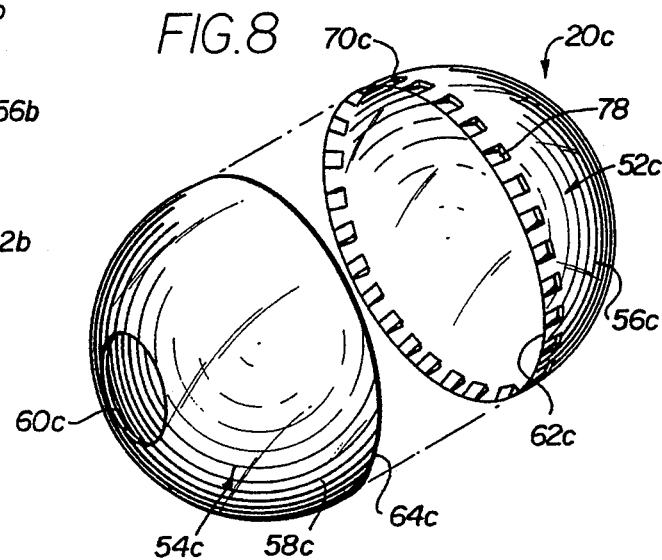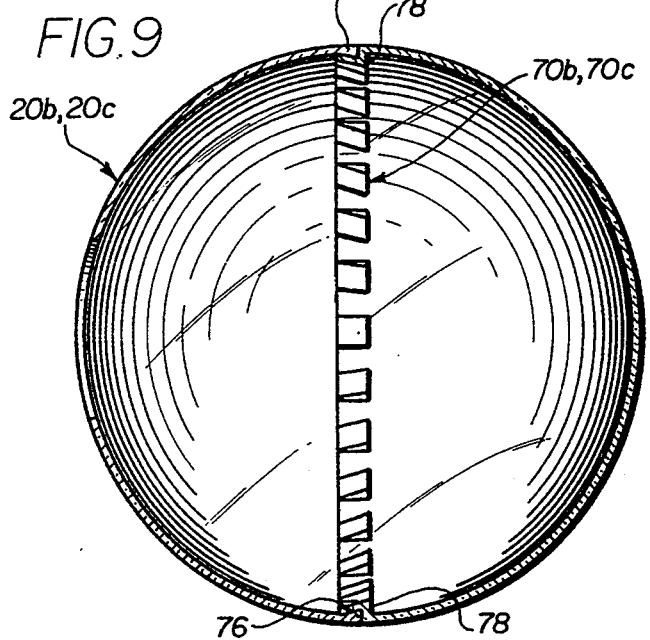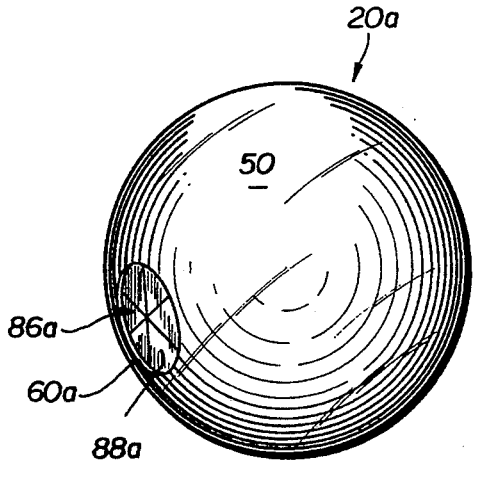

DISPOSABLE CONTAINER FOR CLEANING AND LUBRICATING A DENTAL HANDPIECE

This application is a Continuation-In-Part of pending application, Method and Apparatus for Cleaning and Lubricating a Dental Handpiece, which was filed on Feb. 22, 1993, Ser. No. 08/020,659, U.S. Pat. No. 5,316,590.

BACKGROUND OF THE INVENTION

The present invention generally relates to method for cleaning and lubricating a dental handpiece and to an apparatus which may be employed in this method. More specifically, the invention relates to a disposable container that prevents materials that are expelled from the handpiece during cleaning or lubrication from entering the atmosphere.

Current standards of dental practice require sterilization of dental handpieces between patients. However, the handpiece must be cleaned before going into the sterilizer. This usually includes cleaning the turbine and internal parts. In normal procedures, a cleaning fluid is circulated throughout the dental handpiece by connecting the handpiece to a suitable supply of cleaning fluid and energizing the handpiece. The cleaning fluid and any residue which are expelled through the head of the handpiece escape into the atmosphere. Additionally, after the sterilization of the handpiece has been completed, the handpiece will usually require lubrication. Again, the handpiece is connected to a suitable supply of lubricating fluid and energized. Any excess lubricating fluid which is expelled through the head escapes into the atmosphere.

Dental professionals have started using elaborate devices that flush, disinfect and lubricate the handpiece. However, this merely creates another device which must be cleaned and disinfected or sterilized. Furthermore, such devices are often expensive.

The present invention presents a novel apparatus and method intended to minimize these problems, as well as to present several other improvements.

OBJECTS AND SUMMARY OF THE INVENTION

A general object of the present invention is to provide an apparatus and method for cleaning and lubrication a dental handpiece.

Another object of the present invention is to provide an apparatus and method for capturing materials expelled from the head of a dental handpiece during cleaning or lubrication.

Briefly, and in accordance with the foregoing, the present invention comprises a novel apparatus and method for cleaning and lubricating a standard dental handpiece. The apparatus comprises a disposable container which completely encloses a head of the dental handpiece. When the handpiece is cleaned or lubricated with cleaning or lubricating agents, the container collects the cleaning or lubricating agents and any other materials which are expelled therewith from the handpiece and prevents the expelled materials from entering the atmosphere.

BRIEF DESCRIPTION OF THE DRAWINGS

The features of the invention which are believed to be novel are set forth with particularity in the claims. The organization and manner of operation of the invention, together with further objects and advantages thereof, may best be understood by reference to the following description, taken in connection with the accompanying drawings, wherein like reference numerals identify like elements and in which:

FIG. 1 is a perspective view of a dental handpiece and apparatus according to a preferred embodiment of the present invention;

FIG. 2 is a perspective view of the apparatus of FIG. 1 in an open position;

FIG. 3 is a top view of the apparatus of FIG. 1 in an open position;

FIG. 4 is a view of several apparatuses according to the present invention shown in a nested configuration;

FIG. 5 is a cross sectional view showing the embodiment of FIG. 1 in a closed condition;

FIG. 6 is a perspective view of a dental handpiece and apparatus according to a second embodiment of the present invention;

FIG. 7 is a perspective view of an apparatus according to a third embodiment of the present invention;

FIG. 8 is a perspective view of an apparatus according to a fourth embodiment of the present invention;

FIG. 9 is a cross sectional view showing the embodiments of FIG. 6 or 7 in an assembled condition, and FIG. 10 is a simplified perspective view of the apparatus of FIG. 6 showing a modified form of an opening.

DETAILED DESCRIPTION OF THE ILLUSTRATED EMBODIMENT

While the invention may be susceptible to embodiment in different forms, there is shown in the drawings, and herein will be described in detail, specific embodiments with the understanding that the present description is to be considered an exemplification of the principles of the invention, and is not intended to limit the invention to that as illustrated and described herein.

Referring initially to FIGS. 1 and 6, the apparatus of the invention may be embodied in a container 20, 20a which is used to capture materials 22 that are expelled from the head of a dental handpiece 24 during cleaning or lubrication. This prevents such materials from entering the atmosphere or at least minimizes the amount of such materials. The container 20 is used with a standard dental handpiece 24 that generally includes a handle 26, a head 28 with an opening 30, a turbine 32 housed in the opening 30 of the head 28 and fluid conduit means 34a and 34b which include connective fittings 36 extending from a rear portion 38 of the handpiece 24 for passing fluid from a supply means 40 through the handpiece 24 to the head 28 and turbine 32. In normal use, a fluid such as compressed air is delivered through the conduit 34a to energize the turbine 32, i.e., cause the turbine 32 to rotate. Conduit 34b acts as an air exhaust conduit. Other conduits, such as a water conduit 42 may also be provided. Water conduit 42 has an exit 44 adjacent the head 28.

The container 20 may take any of several forms. In the preferred embodiment, as shown in FIGS. 1-5, the container 20 has two dome-shaped or concave hollow walls 46,48 that are snapped together to form a complete container 20. The container 20 is sized to completely enclose the head 28 of the dental handpiece 24 while leaving enough space to receive fluids and other materials 22 expelled from the head 28 during cleaning or lubrication.

As shown in FIG. 6, the container 20a may be provided as a single piece defined by an exterior wall 50. In FIGS. 7 and 8, the container 20b, 20c is made of two separate hollow hemispheres 52b, 54b and 52c, 54c defined by walls 56b, 58b and 56c, 58c that can be snapped together or otherwise inter-engaged to form a complete container 20b, 20c, respectively, which is generally shaped as a sphere. The embodiments of FIGS. 1, 7 and 8 are preferable in that they will allow for easier bulk packaging and storage, since the concave walls or hemispheres can be nested or stacked, as shown, for example, in FIG. 4.

The container 20, 20a, 20b, 20c may be made of a suitable plastic material or the like. Advantageously, the container is designed to be simple and inexpensive and readily disposable after a single use.

In the preferred embodiment shown in FIGS. 1-5, rims 62, 64 extend radially outwardly from peripheral edges of the two generally concave walls 46, 48. Similarily, in FIGS. 7 and 8, the hemispheres 52b, 54b and 52c, 54c terminate in rims 62b, 64b and 62c, 64c. In order to form a complete container 20, 20b, 20c, the concave walls 46, 48 or hemispheres 52b, 54b and 52c, 54c are snapped together to form a complete container or sphere. In order to do this, the rims 62, 64; 62b, 64b and 62c, 64c, respectively, are placed in an overlapping relation and secured by interlocking means 70, 70b, 70c.

The interlocking means 70, 70b, 70c may take one of many forms. In the preferred embodiment, as shown in FIG. 1, the interlocking means 70 includes a protruding annular ring 72 about the rim 62 and a complementarily shaped annular recess 74 about the rim 64 which receives the protruding annular ring 72 therein when the rims 62, 64 of the concave walls 46, 48 are snapped together. In the embodiments of FIGS. 7 and 8, a series of spaced protruding nibs 76 are provided along the interior of the circular periphery of the rims 64b, 64c and a series of spaced recessed portions 78 that are complementary to the protruding nibs 76 are provided along the exterior of the circular periphery of the rims 62b, 62c. In order to snap the two hemispheres 52b, 54b and 52c, 54c together, the two rims 62b, 64b and 62c, 64c are placed in an overlapping relationship and the series of recessed portions 78 accepts the series of protruding nibs 76 therein.

Each of the embodiments has a through opening or aperture 60, 60a, 60b, 60c thereon which is sized for receiving the head 28 of a dental handpiece 24 therethrough. In the embodiment of FIG. 1, the aperture 60 is located in a shallow, generally cylindrical projecting portion 68 formed on the concave wall 48. In FIG. 7, respective halves 80 and 82 of the aperture 60b are located on each hemisphere 52b and 54b along each rim 62b and 64b. When the two hemispheres 52b and 54b are snapped together, the halves 80 and 82 of the aperture 60b must be aligned to allow the dental handpiece 24 to enter into the container 20b. In FIG. 8, the aperture 60c is located at the bottom portion of a hemisphere 54c approximately centered relative to the circular rim 64c of the hemisphere 54c. The aperture 60b, 60c may be located in other positions relative to hemispheres 52, 54 or otherwise divided between the two hemispheres 52, 54 without departing from the invention.

The apertures 60, 60a, 60b, 60c may include integral closure or sealing means such as a segmented flexible membrane 86, 86a (FIG. 10). The membrane 86 may take on any of several forms. In the preferred embodiment, as shown in FIG. 1, the membrane 86 is comprised of a plurality of substantially identical, generally triangular or wedge-shaped flexible fingers or segments 88 which are symmetrically formed and located and define a small central aperture 90. The membrane 86a of FIG. 10, is similar to the membrane 86 of FIG. 1, having segments 88a, however there is no central aperture 90. The membrane 86, 86a will tend to form at least a partial seal around the handle 26 of the handpiece 24. When the head 28 is inserted, the membrane 86, 86a will flex around the shape of the head 28 and allow it to pass through. Once the head 28 passes through, the membrane 86, 86a generally closes about the handle 26. Thus, the aperture 60, 60a will be in close engagement with handle 26 such that the material 22 that is expelled from the handpiece 24 will tend not to escape the container.

The head 28 of the handpiece 24, when inserted into the container 20, will be completely enclosed. A portion of the handle 26 will be inserted into the container 20, however, a portion of the handle 26 will also extend outwardly of the container 20 through the opening 90. The container 20 encloses the head 28 in such a manner such that the container 20 only contacts the handpiece 24 along the handle 26.

Another feature that may be included in the design of the disposable container is a hinge or hinges 92, 92b as shown in FIGS. 1 and 7, respectively, which may also be used in the embodiment of FIG. 8. The hinge or hinges 92, 92b may be made of a resilient material or pliable plastic or may be molded or otherwise formed as an integral part of and connecting the concave walls 46, 48 or the hemispheres 52b, 54b, respectively. In the embodiment of FIGS. 1-5, the hinge 92 is formed interconnecting outer peripheral edge portions of the rims 62, 64 at one side thereof and facilitates alignment of the locking rings 72, 74 for assembly of the container 20. In FIG. 7, the hinge or hinges 92b facilitates the aligning of the halves 80, 82 of the aperture 60b, and also of the hemispheres 52b and 54b generally for engagement of the interlocking means 70b for assembly of the container 20. The hinge or hinges 92, 92b will also prevent a single concave wall 46, 48 or hemisphere 52, 54 from being misplaced and retain the concave walls and hemispheres in properly matched pairs. This also facilitates stacking of the containers 20, as shown in FIG. 4, for ease of handling and storage, packaging, and the like.

The design of the embodiments of FIGS. 1-5, 7 and 8 presents several advantages. One of these advantages is that the containers are easily and quickly manufactured in a simple and economical process, such as vacuum molding. Also, the ability to nest the containers, as described hereinabove, allows for easier stacking and shipping and prevents a concave wall or hemisphere from being lost. Furthermore, since the container is disposable, it does not have to be cleaned in any further processes.

Having disclosed the construction of the container 20, a method of cleaning and lubricating a dental handpiece will now be discussed. When using the embodiments of FIGS. 1, 7 or 8, the container 20, 20b, 20c is first assembled as described hereinabove.

Next, the head 28 of the dental handpiece 24 and part of the handle 26 are inserted into the container. In doing so, the membrane 86 (if one is provided) flexes as the head 28 passes through and then conforms (e.g. at opening 90) generally to the shape of the handle 26.

The dental handpiece 24 is attached by the fittings 36 to a cleaning fluid supply means 40. The handpiece 24 is then energized. The fluid containing cleaning agents is drawn out of the supply means 40 through the conduit 34 to the head 28 and turbine 32. When the fluid enters the head 28 and turbine 32, excess cleaning fluid and other materials 22 that have amassed on the dental handpiece 24 will be expelled through the head 28 and from the turbine 32. The container catches all of the excess cleaning fluid and materials 22 along its inner surface. Thus, the excess cleaning fluid and materials 22 are not expelled into the atmosphere. Cleaning fluid may also be fed through water conduit 42 and expelled at its outlet 44 to be captured in the container.

Alternatively, the dental handpiece 24 may be completely immersed in a cleaning fluid. Thereafter, the handpiece 24 is attached to an air supply means and energized. When the air enters the head 28 and turbine 32, excess cleaning fluid and other materials 22 are expelled and the container catches the excess cleaning fluid and materials 22 as described hereinabove. As yet another alternative, the head 28 of the dental handpiece 24 may be immersed in a cleaning fluid and the cleaning fluid energized ultrasonically. The handpiece 24 is then attached to an air supply means and energized. Excess cleaning fluid and other materials 22 are expelled and the container catches the excess cleaning fluid and materials 22 as described hereinabove.

When the handpiece 24 has been cleaned, the handpiece 24 is de-energized and removed from the container. The container is then thrown away. Thereafter, the dental handpiece 24 is sterilized.

After sterilization, the handpiece 24 may be lubricated. In order to prevent excess lubricant from being expelled into the atmosphere, a second container is applied to the handpiece in the same fashion as described above with reference to the cleaning process.

The dental handpiece 24 is then attached by the fittings 36 to a lubricant supply means. Alternatively, spray aerosol means or a pump container may be used to apply lubricant to the fittings 36, or directly to the head 28 and turbine 32. The second container is then applied and the handpiece 24 is energized. Lubricant applied at the fittings 36 is drawn through the conduit 34 to the head 28 and turbine 32. Excess lubricant at the head 28 and turbine 32 will be expelled through the head 28 and from the turbine 32. The second container catches the excess lubricant along its inner surface. Thus, the excess lubricant is not expelled into the atmosphere.

When the handpiece 24 is lubricated, the handpiece 24 is de-energized and removed from the container. The container is then thrown away. The dental handpiece 24 is now ready for use.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiments and specific construction described herein but should be defined by the appended claims and equivalents thereof. Accordingly, the aim in the appended claims is to cover all such changes and modifications as fall within the true spirit and scope of the invention The invention is claimed as follows:

1. An apparatus for use with a dental handpiece, said dental handpiece having a handle portion and a head portion mounted to said handle portion, said head portion having means therein for mounting a turbine, a turbine mounted in said head portion and fluid conduit means in the handle portion communicating with the head portion for carrying fluid for driving said turbine, said apparatus being used when said dental handpiece is being cleaned or lubricated by respective cleaning or lubricating fluid being circulated through the fluid conduit of the handle portion to the head portion and turbine, said apparatus comprising:

a disposable container sized for surroundingly enclosing a head portion of a dental handpiece, said container having an aperture sized to receive a head portion of a dental handpiece therethrough for entry of the head portion into the container so as to be substantially surrounded by the container while leaving part of a handle portion of the dental handpiece extending outwardly of the container so that when cleaning or lubricating fluid is circulated through the fluid conduit of the handle portion to the head portion and turbine, that part of said fluid which is expelled from the head portion, together with any other materials carried by the fluid, are received and confined along an inner surface of the container.

2. The apparatus as defined in claim 1, wherein the container is defined by wall means of size and configuration to completely surround and enclose the head portion of the handpiece, said wall means also defining said aperture dimensioned and located for surrounding the handpiece along the handle portion.

3. The apparatus as defined in claim 1, wherein the container is generally spherical in shape.

4. The apparatus as defined in claim 1, wherein the container comprises two container portions, and attachment means for joining the two container portions together.

5. The apparatus as defined in claim 4, wherein the attachment means comprises a hinge integral with two container portions.

6. The apparatus as defined in claim 1, wherein the container is comprised of two container portions, each container portion being generally dome-shaped.

7. The apparatus as defined in claim 6, wherein a shallow, generally cylindrical projecting portion extends from one of said container portions, and wherein said means defining the aperture is formed in said projecting portion.

8. The apparatus as defined in claim 1, wherein the container is comprised of two container portions, each container portion being generally hemispherical in shape.

9. The apparatus as defined in claim 1, wherein the container is comprised of two container portions, each container portion having formed thereon complementary engagement means for joining the two container portions together.

10. The apparatus as defined in claim 9, wherein the complementary engagement means includes a radially outwardly projecting rim portion on each portion, a protruding annular ring along the rim portion of one container portion and a complementarily shaped annular recess along the rim portion of the other container portion for receiving the protruding annular ring therein.

11. The apparatus as defined in claim 9, wherein the complementary engagement means includes a peripheral rim portion on each of said container portions, a series of spaced protruding nibs along the rim portion of one container portion and complementarily shaped recesses along the rim portion of the other container portion for receiving the protruding nibs therein.

12. The apparatus as defined in claim 1, wherein the container is comprised of two container portions, a portion of the means defining the aperture being formed in each of the container portions.

13. The apparatus as defined in claim 1, wherein the means defining the aperture includes sealing means for creating a seal around the handle portion.

14. The apparatus as defined in claim 13, wherein said sealing means includes a plurality of wedge-shaped flexible segments integral with said container and projecting into said aperture.

15. The apparatus as defined in claim 14, wherein said plurality of wedge-shaped flexible segments define a further smaller aperture aperture in the center thereof.

16. The apparatus as defined in claim 1, wherein cross sectional dimensions of the aperture in the container are at least as great as cross sectional dimensions of the head portion of the dental handpiece.

17. The apparatus as defined in claim 1, wherein the container is formed from a plastics material.

* * * * *